United States Patent [19]

Blaschke et al.

[11] Patent Number: 4,848,145
[45] Date of Patent: Jul. 18, 1989

[54] IN-SITU LINEAR FLOW PROPPANT CONDUCTIVITY TEST CELL

[75] Inventors: Keith E. Blaschke; James W. Mueller, both of Duncan, Okla.

[73] Assignee: Halliburton Company, Duncan, Okla.

[21] Appl. No.: 247,997

[22] Filed: Sep. 21, 1988

[51] Int. Cl.$^4$ .......................................... E21B 43/267
[52] U.S. Cl. ......................................... 73/153; 73/38; 73/865.6
[58] Field of Search .................... 73/38, 151, 153, 155, 73/865.6; 166/250, 280

[56] References Cited

U.S. PATENT DOCUMENTS

| | | | |
|---|---|---|---|
| 4,304,122 | 12/1981 | Tentor | 73/38 |
| 4,537,063 | 8/1985 | Barnaby | 73/38 |
| 4,555,934 | 12/1985 | Freeman et al. | 73/38 |
| 4,562,726 | 1/1986 | Barnaby | 73/38 |
| 4,572,009 | 2/1986 | Brauer et al. | 73/38 |
| 4,587,857 | 5/1986 | Bush | 73/863 |
| 4,599,891 | 7/1986 | Brauer et al. | 73/38 |
| 4,691,558 | 9/1987 | Vinson et al. | 73/64.1 |
| 4,734,649 | 3/1988 | Barnaby | 324/376 |
| 4,791,822 | 12/1988 | Penny | 73/38 |

OTHER PUBLICATIONS

G. S. Penny, "An Evaluation of the Effects of Environmental Conditions and Fracturing Fluids Upon the Long Term Conductivity of Proppants", SPE Paper No. 16900, Sep. 1987, pp. 229–244.

M. A. Parker, B. W. McDaniel, "Fracturing Treatment Design Improved by Conductivity Measurements Under In-Situ Conditions", SPE Paper 16901, Sep. 1987, pp. 245–254.

M. G. Much and G. S. Penny, "Long-Term Performance of Proppants Under Simulated Reservoir Conditions", SPE/DOE Paper 16415, May 18, 1987, pp. 257–266.

G. E. Cooke, Jr., "Conductivity of Fracture Proppants in Multiple Layers", Journal of Petroleum Technology, Sep. 1973, pp. 1101–1107.

Primary Examiner—Stewart J. Levy
Assistant Examiner—Kevin D. O'Shea
Attorney, Agent, or Firm—Mark E. McBurney; J. A. Walkowski

[57] ABSTRACT

An in-situ linear flow proppant conductivity test cell is provided which allows a downhole fracturing operation to be accurately simulated under laboratory conditions. The test apparatus includes a housing, having pistons therein, a plurality of heating elements, and a packer with a plurality of ports therethrough. Core samples are inserted into the test apparatus and a proppant bed, such as a sand slurry, is introduced into the test cell between the core samples. An external press then provides pressure to the pistons simulating the overburden experienced downhole, while the heating elements simulate downhole temperatures. Pressure, differential pressure, flow rate temperature and fluid loss characteristics can then be measured through the plurality of ports within the packer.

16 Claims, 6 Drawing Sheets

IN-SITU LINEAR FLOW PROPPANT CONDUCTIVITY TEST CELL

BACKGROUND OF THE INVENTION

In the oil and gas industry it is often desirable to stimulate a well by introducing a high pressure proppant laden fluid into the well bore. The fluid may include water or diesel, which may be in the form of a gel or foam, while the proppant may commonly be sand or bauxite, although many other proppants are known and used.

Pressures on the order of 5,000 to 12,000 psi are often required to fracture a formation and are supplied by above ground pumping equipment such as a HT-400 triplex pumping unit as illustrated on pages 2414, 2415 and 2418 of Halliburton Services Sales and Service Catalog, volume 43.

After the formation is fractured, the proppant remains in the fracture itself, while the fluid is retrieved, or allowed to dissipate within the formation. The proppant then acts to hold the fracture open such that a channel is maintained which enhances the flow of hydrocarbons from the producing formation to the well bore. The success of the stimulation operation often depends upon the ability of the proppant to maintain the fracture in an open position. Therefore, it would be desirable to have a laboratory testing unit which will simulate a fracturing operation and provide results prior to the actual stimulation operation. In particular, an in-situ test cell which could utilize actual core samples and simulate actual downhole temperature, permeability, conductivity and fluid migration characteristics would be extremely useful to the oil and gas service industry.

In a paper prepared for a joint Society of Petroleum Engineers/Department of Energy Symposium entitled "Long-Term Performance of Proppants Under Simulated Reservoir Conditions", number 16415, by M. G. Mach and G. S. Penny, a standard American Petroleum Institute test cell has been modified for use in in-situ type conditions. FIG. 1 illustrates how holes were drilled into the pistons and how ring type seals are used to seal around the piston. Further, a glue type sealant must be used to prevent fluid loss from occurring around the outside edge of the core samples.

Additionally, U.S. Pat. No. 4,562,726 to Barnaby shows an apparatus for testing the compressability of a single formation core sample. The test apparatus includes a sleeve which seals the core sample when pressurized fluid is supplied to a surrounding annular space. Similarly, Braver et al, U.S. Pat. No. 4,599,891, describes a core holder for a single core sample having a sleeve which seals the sample when pressurized fluid is introduced to the surrounding annulus and a radial force is applied therearound. The sleeve provides a seal around the core, moveable plug and a fixed plug.

Therefore, a need exists for a device such as the present invention, as described herein, which utilized a settable packer to seal around the core samples, pistons and proppant bed such that more reliable results are obtained than are presently possible with the prior art test devices.

SUMMARY OF THE INVENTION

Broadly, the present invention allows a proppant bed to be placed between two actual core samples taken from the well bore of interest, or core samples from a representative formation similar to the formation being fractured.

Hydraulic pistons provide the force which simulates the overburden, or formation pressure as it closes the core samples on the proppant bed. Further, actual formation temperatures can be simulated due to a plurality of heaters which are provided in the test cell. Fluid loss is allowed through the core samples such that actual fluid loss characteristics can be tested.

A settable packer is also provided which seals the pistons, core samples and proppant bed thus preventing any migration of fluid therebetween. This packer maintains a seal while the pistons, core and proppant bed are in motion, such as during proppant bed loading.

Further, the packer includes a plurality of ports which allow fluid to flow through the proppant bed, and measurement of the proppant bed temperature, differential pressure and fluid flow rate.

Therefore, in accordance with the previous summary, objects, features and advantages of the present invention will become apparent to one skilled in the art from the subsequent description and the appended claims taken in conjunction with the accompanying drawings.

DETAILED DESCRIPTION OF THE PREFERRED EMBODIMENTS

Figure 1:
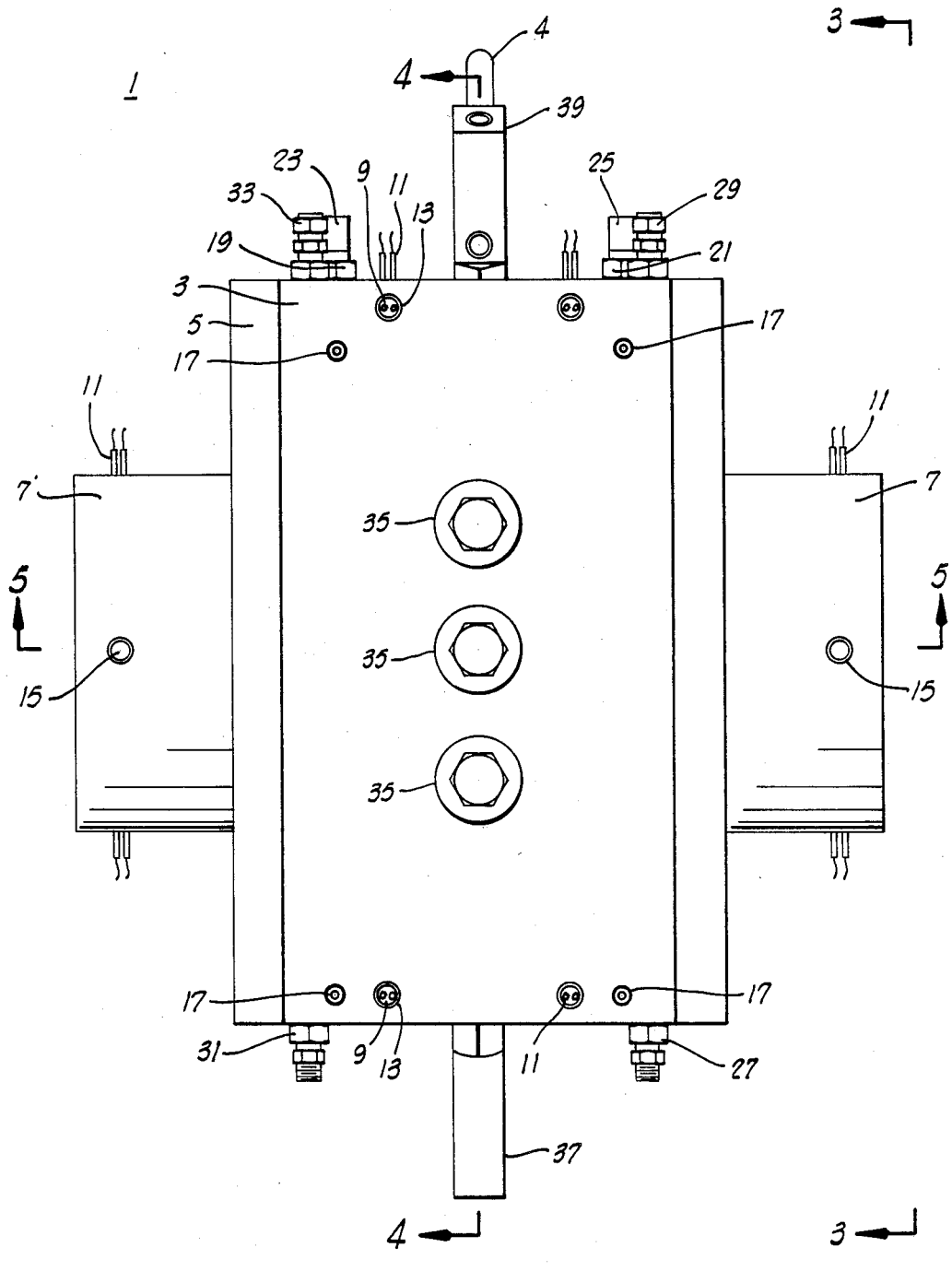
FIG. 1 is a front elevational view of the in-situ proppant test cell of the present invention.

Referring to FIG. 1, a front elevational view of an in-situ linear flow proppant conductivity test cell is shown and generally depicted by reference numeral 1. A housing 3 having end-caps 5 make up the body of test cell 1. Lifting eye 4, which is attached at threaded hole 6 (FIG. 4), allows the test cell 1 to be easily moved and is connectable to the opposite side of test cell 1 by threaded engagement, or the like, at hole 8. Housing 3 and end caps 5 are preferably constructed from a high yield strength material such as Inconel 718.

Figure 2:
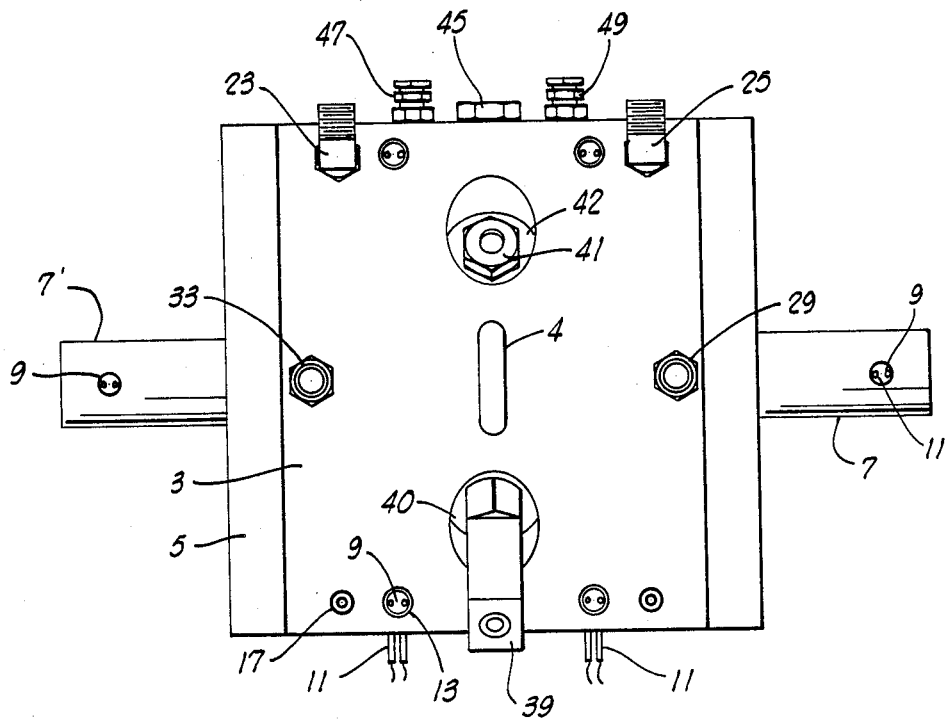
FIG. 2 is a top plan view of the test cell depicting various features thereon.

Pistons 7, and 7' are also constructed from a high yield strength material, such as Inconel 718. Pistons 7, 7' apply pressure to core samples 121, 122 (FIG. 5), having inside surfaces and 121' and 122', respectively and which are in communication with the proppant bed (described below), in order to simulate downhole overburden pressures. Insertable resistive electric heaters 9, having external leads 11, are placed within holes 13 drilled into housing 3 and pistons 7, 7' (FIG. 2). Fluid loss ports 15 are present in pistons 7, 7' and allow fluid to migrate through core samples 121, 122 in the same manner as an actual fracturing operation.

Figure 4:
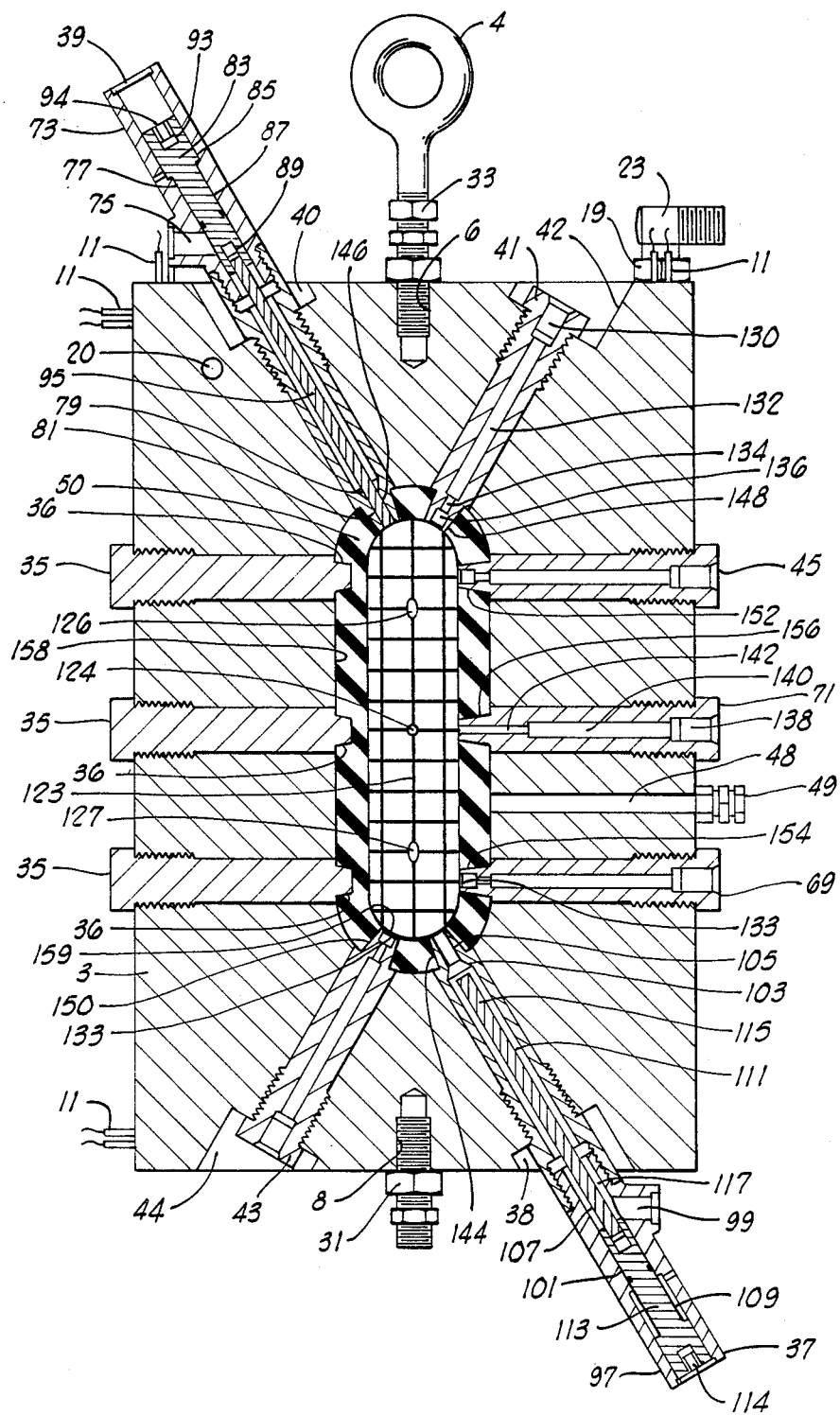
FIG. 4 is a vertical crossectional view of the test cell taken along line 4—4 of FIG. 1, showing the packer crossection having ports therethrough.

Coolant, typically water or air, is circulated through housing 3 within a series of connected drilled holes 20 (FIG. 4).

Plugs 17 are used to close drilled ends of the coolant holes 20 which were created during fabrication.

Coolant ports 19 and 21, having fittings 23 and 25, respectively, allow the coolant source to be connected such that circulation through housing 3 can occur.

A settable packer 50 (FIG. 7) is utilized to provide a sealing engagement between the pistons, core samples and proppant bed. Setting rings 160,162 (FIG. 5) are used to set the packer 50 in response to hydraulic pressure which is provided through a first insert setting port 27 having first vent 29 such that air can be removed during setting of the packer 50. Second insert setting port 31 and second vent 33 operate in precisely the same manner as port 27 and vent 29. Retaining inserts 35 extend through housing 3 and contact the settable packer 50 to initially hold the packer in place, prior to setting.

Proppant valves 37 and 39 are insertable into proppant slurry ports 38 and 40 (FIG. 4) and are used to place the proppant slurry into the test cell, simulating in-situ conditions. The settable packer 50, proppant valves 37, 39, inserts and the operation of the test cell 1 will be described in detail below.

A top plan view of test cell 1 is shown in FIG. 2. Like reference numerals in FIG. 2 and throughout the remainder of the description refer to the same components of test cell 1 as previously described.

A recessed filtered flow insert 41 is shown which allows fluid contained in the proppant slurry to be removed, simulating the fluid flow back aspects experienced in an actual fracturing operation. Filtered flow insert 41 is insertable into fluid exit port 42. Similarly, in FIG. 4, filtered flow insert 43 is insertable into fluid exit port 44. A first pressure insert 45 is shown in FIG. 2 and will be more fully described with reference to FIG. 4. Packer unsetting ports 46 and 48 are depicted on the same side of test cell 1 as first pressure insert 45. Packer unsetting ports 46, 48 have fittings 47 and 49, respectively, which allow pressurized hydraulic fluid, such as water, to be introduced which will aid in the removal, or unseating of settable packer 50.

Figure 3:
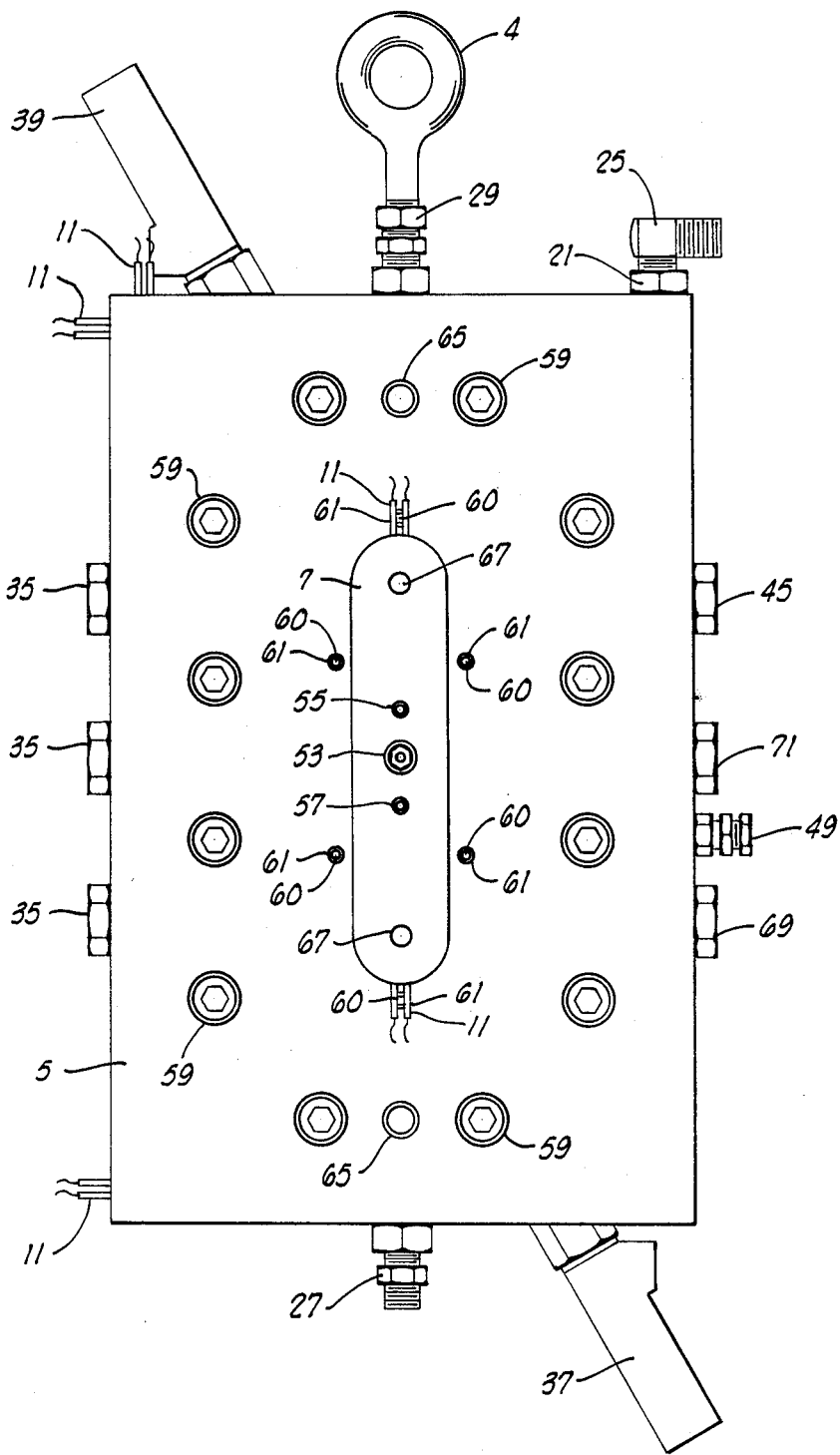
FIG. 3 is a right side elevational showing a piston, port outlets and other components of the present invention.

FIG. 3 is a right side elevational view of the present invention further showing the elements of test cell 1. Piston 7 is shown as including a plug 53 which diverts fluid to fluid loss port 15. Also, piston 7 includes vents 55, 57 which allow air pressure to be relieved as heaters 9 are inserted. A plurality of threaded connectors 59, such as allen or hexagonal head bolts, or the like, are used to attach end cap 5 to housing 3. Next, a plurality of threaded holes 61 are shown for receiving screws 60 which attach an end cap seal 63 (FIG. 5) to end cap 5. Holes 65 are threaded to allow a bolt to be inserted therein, such that a force can be applied to housing 3 separating housing 3 and end cap 5, which can become stuck together during a testing operation. Similarly, threaded holes 67 allow a piston pulling device (not shown) to be attached thereto so that pistons 7 can be removed from test cell 1.

A second pressure insert 69 as well as a temperature insert 71 are shown in FIG. 3 and will be described in detail with regard to FIG. 4.

FIG. 4 is a crossectional view of the present invention taken along line 4—4 of FIG. 1. Proppant valve 39 includes a two-piece outer body 73 having a proppant input port 75 therethrough. Outer body 73 defines a substantially cylindrical first inner surface 77, frustoconical surface 79 and second cylindrical surface 81. A two-piece stem 83 having a first and second outer surfaces 85, 87 is threadedly disposed within body 73.

Second outer surface 87 of stem 83 is adjacent first inner surface 77 and has a smaller diameter than the diameter of cylindrical surface 77. Thus, an annular area 89 is created and in communication with proppant input port 75. Proppant slurry can be introduced into test cell 1 by pumping into input port 75 down annular area 89, through frustoconical area 79, second cylindrical area 81 and into the test area 91 (FIG. 5) of test cell 1.

A first end 93 of stem 83 includes an allen head fitting 94, or the like such that stem 83 can be adjusted inward. The second end 95 of stem 83 is insertable into the second cylindrical surface 81, via first conical surface 79. The outside diameter of second end 95 is minutely less than the diameter of second cylindrical surface 81 such that fluid may flow around the annulus formed between second end 95 and second cylindrical surface 81, however proppant material, such as sand, is prevented from flowing therethrough.

Proppant valve 37 is structurally and functionally identical to valve 39 and includes outer body 97, proppant input port 99, first cylindrical surface 101, frustoconical surface 103, second cylindrical surface 105, stem 107 having first and second surfaces 109, 111 and first and second ends 113, 115. An annular area 117 is defined between second cylindrical surface 105 and the outside diameter of second surface 111.

Figure 5:
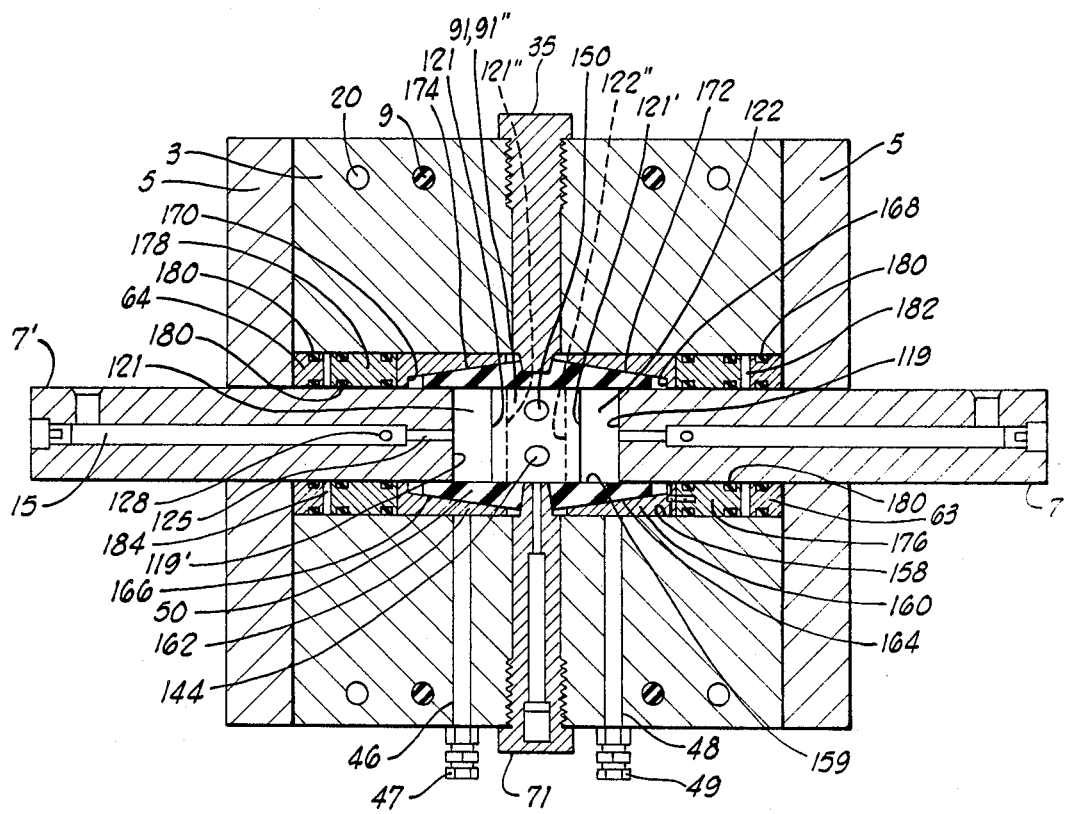
FIG. 5 is a horizontal crossectional view taken along line 5—5 of FIG. 1 depicting a crossection of the test cell showing the packer with pistons therein.

Piston 7' includes an inner surface 119' which is in communication with core sample 121 and provides pressure thereto. A pattern of grooves 123 of a "V" configuration are cut linearly into the face of surface 119', which is adjacent to core sample 121. A hole 124 provides an entrance to fluid chamber 125 (FIG. 5) which is in communication with fluid loss port 15. Similarly, holes 126, 127 provide an entrance to fluid chambers (not shown) which are also in communication with fluid port 15 forming a "Y" or crows' foot shaped configuration therewith. More particularly, fluid flowing into hole 127, drains into fluid port 15 at hole 128 (FIG. 5). A single piston 7', which is shown on the left side of FIG. 5 has been described, however, the right piston 7 is structurally and functionally identical to the described piston 7'.

Actual downhole fluid loss characteristics of core samples 121, 122 can be simulated since the fluid contained in the proppant slurry can migrate through, for example, core sample 121 into grooves 123, holes 124, 126, 127 and fluid loss port 15. Thus, the quantity of fluid lost through core 121 and its rate can be measured as it leaves port 15.

Figure 8:
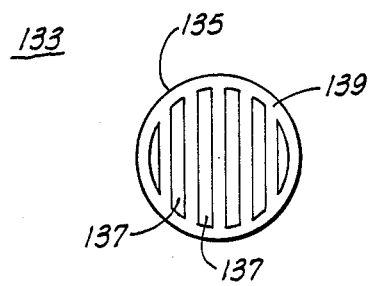
FIG. 8 is a plan view of a grate, used in the present invention, which allows fluid to pass but screens proppant material.

Filtered flow insert 41 defines a first cylindrical volume 130 and second cylindrical volume 132. Further, a neck portion 134, also cylindrically configured, connects second volume 132 with a third cylindrical volume 136. Volume 136 is in communication with test area 91, however an insertable grate 133 (also see FIG. 8) is disposed therebetween. The grate 133 allows fluid from the proppant slurry to flow through cylindrical volumes 130, 132, 136 and neck portion 134 so that the migration of fluid through a formation, which occurs during an actual fracturing, flow back and production operations, can be simulated. The grate 133 has a cylindrical outer surface 135 and fluid passage slots 137 defined within front surface 139. Slots 137 are of such a dimension that proppant material is prevented from flowing therethrough, however fluid is allowed to pass. Inserts 41, 43, 45 and 69 each include a grate 133 inserted therein so that fluid may pass therethrough but the entrained proppant is screened out.

Filtered flow insert 43, first pressure insert 45 and second pressure insert 69 are all structurally identical to insert 41. Temperature insert 71 includes a first cylindrical volume 138, second cylindrical volume 140 and third cylindrical volume 142 such that a temperature probe can be inserted therein. Furthermore, it will be appreciated by one skilled in the art that retaining inserts 35, proppant valves 37, 39, filtered flow inserts 41, 43, pressure inserts 45, 69 and temperature insert 71 are all engaged with housing 3 by a threaded connection, or a similar manner as is known in the art.

Packer 50 is constructed of an elastomeric material, or the like, and has a generally elliptical crossection. Retaining recesses 36 provide an area which retaining inserts 35 are insertable into, thereby allowing engagement between packer 50 and inserts 35. Proppant ports 144, 146 allow proppant valves 37, 39 respectively to communicate with and deliver proppant slurry to test area 91. Fluid ports 148, 150 allow fluid to pass between filtered flow inserts 41, 43 respectively, and test area 91. Pressure sensing ports 152, 154 provide a path for pressure to be communicated from test area 91, through inserts 45, 69, respectively, to an externally connected pressure transducer (not shown), which measures the difference in pressure between first pressure insert 45 and second pressure insert 69. Finally, temperature sensing port 156 communicates the temperature within test area 91, i.e. the proppant bed, through a temperature probe, within insert 71, to an externally connected temperature sensor (not shown).

Next, the setting of packer 50 and the sealing arrangement within test cell 1, will be described with reference to FIG. 5 which is a crossectional view of the present invention taken along line 5—5 of FIG. 1.

As can be seen from FIG. 5, test cell 1 includes an inner area defined by surface 158. Packer 50 surrounds core samples 121, 122 test area 91 and pistons 7 and 7'. A packer inner surface 159 is substantially elliptically configured and corresponds to the outer surfaces of core samples 121, 122, test area 91 and pistons 7 and 7'. Setting rings 160, 162 are elliptically shaped rings having first inside tapered surfaces 164, 166, respectively. Surfaces 164, 166 are angularly disposed such that when rings 160, 162 are slidably inserted and positioned adjacent packer 50, the thickness of rings 160, 162 increases at the edge nearest end caps 5. Second inner surfaces 168, 170 of rings 160, 162, respectively, intersect surfaces 164, 166 forming an obtuse angle therebetween.

First skirt surface portion 172 and second skirt surface portion 174, both of packer 50 are angularly oriented to taper in a direction opposite surfaces 164, 166 of setting rings 160, 162. Thus, when setting rings 160, 162 are inserted they form a wedge against surfaces 172, 174 respectively, of packer 50 thereby sealing piston 7, core samples 121 and test area 91.

In order to hydraulically insert setting rings 160, 162 which set packer 50, piston seals 176, 178 are used. Seals 176, 178 each include O-rings 180, such as those made of an elastomeric material which are well known in the art. Seals 176, 178 provide sealing engagement around pistons 7 and 7', respectively, which is required as setting rings 160, 162 are hydraulically inserted and the hydraulic pressure within test cell 1 increases. Similarly, end cap seals 63, 64 are required to seal between pistons 7 and 7', respectively, housing 3 and end caps 5. Seals 63, 64 each contain o-rings 180 similar to those used in piston seals 176, 178.

As previously noted, hydraulic setting ports 27, 31 (FIG. 1) are used to introduce pressurized hydraulic fluid into chambers 182, 184 of FIG. 5. As chambers 182, 184 fill with hydraulic fluid, vents 29, 33 (FIG. 1) remain open to allow the air within chambers 182, 184 to be released to the atmosphere. Vents 29, 33 are closed when hydraulic fluid starts to be released, thereby allowing hydraulic pressure within chambers 182, 184 to increase and force setting rings 160, 162 to "wedge" against, and to set packer 50. The test may then proceed and the overburden pressure exerted by pistons 7, 7' on core samples 121, 122 can be increased to the level experienced during a normal fracturing operation without any leakage occurring therearound.

After a test is run, problems often occur in disassembling the test cell 1. In particular, it is difficult to remove setting rings 160, 162 after they have been wedged against packer 50. To solve this problem, packer unsetting ports 46, 48 and their associated fittings 47, 49 are used to unseat setting rings 160, 162. Pressurized hydraulic fluid such as water is introduced into ports 46, 48 which contacts piston seals 176, 178 forcing them outward. In order to force setting rings 160, 162 outwardly, a connection between piston seals 176, 178 and setting rings 160, 162 must be made.

Figure 6:
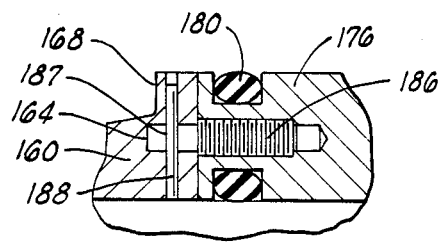
FIG. 6 is a detail of the connection between the piston seal and setting ring of the present invention.

FIG. 6 is a detail illustrating the connection between piston seal 176 and setting ring 160. It should be noted that although a single connection point is shown in FIGS. 5 and 6, numerous connections are contemplated and the preferred embodiment uses six such connections along the circumference of the abutting surfaces of setting rings 160, 162 and piston seals 176, 178. A stud 186, having a hole 187 defined in a first end thereof, is inserted into one of a plurality of holes drilled into piston seal 176 and aligned with one of a corresponding plurality of holes drilled into setting ring 160. Next, a pin 188 is inserted through a perpendicular intersecting hole drilled into setting ring 160 such that pin 188 is inserted into the hole defined in the first end of stud 186.

Figure 7:
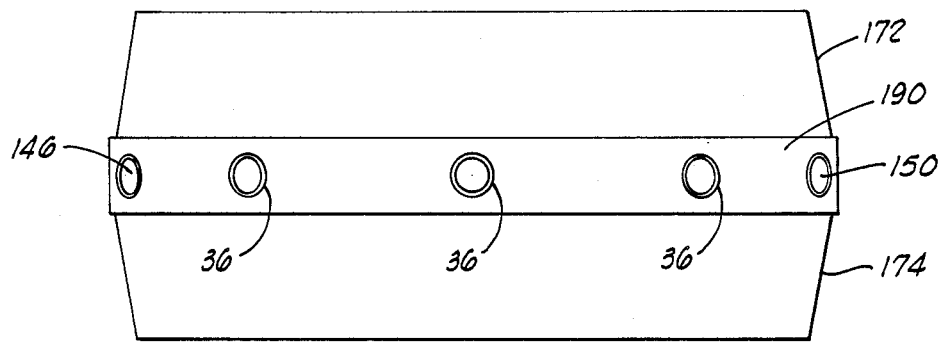
FIG. 7 is an elevational view of the settable packer of the present invention which seals around the materials being tested.

FIG. 7 is an elevational view of packer 50 rotated 90° from its normal vertical orientation in the load cell showing the side thereof which receives retaining inserts 35. Retaining recesses 36 are used to receive inserts 35. Fluid port 150 and proppant port 146 can also be seen in the view of FIG. 7. As previously noted, packer 50 is made of an elastomeric material, or the like, including an inside surface 159 which forms a resilient seal around the proppant bed, core samples 121, 122 test area 91 and pistons 71. Further, a central collar portion 190 surrounds the midsection of packer 50. Collar 190 extends outwardly such that contact is made with inner surface 158 of housing 3 when packer 50 is inserted into test cell 1. Thus, packer 50 further supports the proppant bed when pressure is applied by preventing the proppant bed from bulging outward.

The operation of test cell 1 will now be described with reference to the drawings. First, core samples 121, which have been retrieved from the well bore to be tested, are placed within packer 50, which is placed within test cell 1.

Retaining inserts 35 are then inserted into recesses 36 such that packer 50 is held in place. Similarly, temperature insert 71 is inserted into port 156; filter flow inserts 41, 43 are inserted in ports 148, 150, respectively; pressure inserts 45, 69 are inserted into ports 152, 154, respectively; and proppant valves 37, 39 are inserted into ports 144, 146, respectively. Next, pistons 7 and 7' are inserted into test cell 1 such that inner surfaces 119, 199' contact samples 121, 122, respectively, within packer 50. Setting rings 160, 162 and piston seals 176, 178 are then inserted to set packer 50, as described above. End caps 5 having end cap seals 63, 64 attached thereto are bolted to housing 3 such that pistons 7 extend out of end caps 5.

Test cell 1 can then be placed within an external press (not shown) which provides the overburden, simulating formation pressure. Connections can then be made between pressure inserts 45, 69 and a pressure transducer which provides an electrical signal (representing differential pressure) to an external display. Temperature insert 71 can also be connected to an external display which will output temperature in degree Farenheit.

As can be seen in FIG. 5, core samples 121, 122 are disposed at opposite ends of test area 91 and adjacent pistons 7' and 7, respectively, such that inner surfaces 121' and 122' are facing inwardly. The proppant bed is placed between inner surfaces 121' and 122' such that contact between the proppant material and core sample surfaces is achieved. It is readily apparent that as piston 7, 7' provide overburden pressure to the proppant bed and core samples 121, 122, the volume of the bed and proppant bed, i.e. the volume defined by inner surfaces 121', 122' and a surface 158 will decrease, as shown by core sample inner surface positions 121" and 122", which define reduced test area 91'.

The testing procedures can then be implemented. Initially, a clean fluid is introduced, for example, through proppant valve 37 and into test area 91, between inner surfaces 121', 122'. The other proppant valve 39 is restricted by an external valve or regulator (not shown) in order to maintain pressure within the test cell. During this portion of the test, the clean fluid, such as a 40 lb. gel, is introduced at approximately 1200 psi. This allows the fluid loss characteristics of core samples 121 and 122 to be evaluated. Fluid is forced through core samples 121, 122 and collected from fluid loss port 15 of pistons 7, 7'. Thus, the amount of fluid lost through cores 121, 122 can be measured for a given time period. While the fluid is passing through cores 121, 122 the particulate entrained therein builds up along the inside surfaces 121', 122' of cores 121 and 122 thus creating a filter cake thereon. This filter cake is present during actual fracturing operations, because clean fluid precedes the proppant slurry into the formation and the fluid migrates through the formation. Pistons 7, 7' are maintained at a pressure (overburden) level which counteracts the approximate 1000 psi level of the clean fluid being introduced between surfaces 121' and 122'.

The next step includes introducing a proppant laden slurry, such as 40 lb. gel having 0-30 lbs./gal of proppant entrained therein, into test area a, between surfaces 121' and 122', through proppant valve 37. The other proppant valve 39 is closed, and the fluid within the proppant slurry is removed through filtered flow valve 43, which allows fluid to pass but screens the proppant such that a proppant bed is formed within test area 91 of test cell 1. Next, the press, which may provide up to 15,000 psi of pressure, increases the overburden on pistons 7, 7' to a level corresponding to the well bore being tested. The heaters 9 are also energized to provide temperatures experienced in the test formation. Next, proppant valve 37 is closed and clean fluid is introduced through one of filtered flow inserts 41, 43. Assuming flow insert 41 is used to introduce clean fluid, insert 43 is then used to measure the fluid flow rate by collecting the fluid after it has migrated through the proppant bed. Additionally, an external valve, or regulator (not shown) will be connected to flow insert 43 restricting the flow of clean fluid therethrough. This will effectively pressurize the clean fluid and simulate the static head pressure experienced in an actual well bore due to the column of fluid therein. As pressure and temperature increase, readings are periodically taken through pressure ports 45, 69 and temperature port 71.

Using the known and measured parameters, data including fluid loss of the core sample, proppant bed conductivity, proppant embedment, permeability can be calculated. Therefore, the present invention allows precise measurements to be taken which simulate an actual well bore fracturing operation more accurately than any prior art test cell which is presently known.

Although certain preferred embodiments have been shown and described, it should be understood that many changes and modifications may be made therein without departing from the scope of the appended claims. For example, an elliptical packer, core samples, and pistons are described herein, however, it is readily apparent to one skilled in the art that a circular, or other configuration of these elements will provide the benefits of the present invention. Moreover, a single piston may be used in conjunction with an opposing stationary member, and the tapered surfaces of the packer and packer setting rings may be oriented in opposite directions to the orientation of the preferred embodiment.

What is claimed is:

1. An apparatus for testing formation core samples and a proppant bed, to be used in an oil well fracturing operation, by simulating actual fractured formation conditions, said apparatus comprising:
    a housing, including a plurality of ports defined therein;
    piston means, insertable into said housing, for applying pressure to said core samples and said proppant bed; and
    settable packer means for providing sealing engagement between said piston means, said core samples and said proppant bed, said settable packer means including a plurality of ports defined therein being in communication with said housing ports.

2. An apparatus according to claim 1, further comprising means for heating said core samples and said proppant bed to a temperature level required to simulate said actual conditions.

3. An apparatus according to claim 2 wherein said settable packer means surrounds said core samples and at least a portion of said piston means adjacent to said core samples.

4. An apparatus according to claim 1 wherein said settable packer means further comprises:
    a central collar portion having said packer ports defined therethrough;
    a first skirt portion, extending perpendicularly outwardly from said central collar portion and having a taper such that the outside circumference thereof decreases in a direction away from said central portion; and a second skirt portion, extending perpendicularly from said central collar portion in a direction opposite said first portion and having a taper such that the outside circumference thereof decreases in a direction away from said central portion.

5. An apparatus according to claim 1 wherein said test apparatus further comprises:

packer setting means for providing a force to said settable packer means such that a sealing engagement between said core samples, said proppant bed and said piston means is formed.

6. An apparatus according to claim 5 wherein said housing includes at least one end cap through which said piston means extends into said housing end cap thereon and said packer setting means comprises:

a plurality of setting rings each having an angularly oriented surface proximate to and of an angle corresponding to one of said first skirt portion and said second skirt portion of said settable packer means;

at least one piston seal attached to one of said setting rings and surrounding said piston means for effecting a slidable sealing engagement between said housing and said piston means; and at least one end cap seal to effect a sealing engagement between said end cap and said piston means.

7. An apparatus according to claim 6 wherein said packer setting means further comprises:

at least one packer setting port in said housing for providing pressurized fluid behind said piston seal to force said setting rings against said settable packer means; and at least one packer setting vent which allows air entrapped behind said piston seal to be displaced by said pressurized fluid.

8. An apparatus according to claim 7 wherein said test apparatus further comprises packer unsetting means for disengaging said setting rings from said settable packer means.

9. An apparatus according to claim 8 wherein said packer unsetting means comprises packer unsetting ports, in communication with said piston seal for providing pressurized fluid to move said piston seals in a direction away from said settable packer means to retract at least one of said setting rings and unset said packer means.

10. An apparatus according to claim 1 wherein said piston means comprises:

at least one inner surface in contact with said core samples;

a plurality of fluid loss channels, disposed within said piston means, for allowing a pressurized clean fluid introduced between said core samples, to be removed from said test apparatus; and a plurality of grooves formed into said inner surface for directing said clean fluid into said fluid loss channels, wherein said clean fluid migrates through said core samples to said fluid loss channels such that the fluid loss characteristics of said core samples can be measured.

11. An apparatus according to claim 1 wherein said test apparatus further comprises:

a plurality of retaining inserts, insertable into said housing and engaging said settable packer means for holding said settable packer means;

a plurality of pressure inserts in communication with said proppant bed such that the differential pressure and pressure therein can be externally recorded;

a temperature insert in communication with said proppant bed such that a temperature thereof can be externally recorded;

a plurality of filtered flow inserts for introducing a clean fluid into, and removing said clean fluid from, said test apparatus; and a plurality of proppant valve inserts for introducing a proppant slurry into said test apparatus.

12. An apparatus according to claim 11 wherein said pressure insert and said filtered flow insert each include a grate disposed in an end thereof adjacent said core samples, which grate allows said fluid to pass therethrough but blocks the passage of said proppant.

13. An apparatus for testing formation core samples and a proppant bed by simulating actual conditions, including introducing a proppant slurry and a clean fluid between the core samples, said apparatus comprising:

a housing;

piston means, insertable into said housing, for applying pressure to said core samples and said proppant bed;

packer means for providing sealing engagement between said piston means, said core samples and said proppant bed;

packer setting means for providing a first force to said packer such that said sealing engagement is achieved; and packer unsetting means for providing a second force, in a direction opposite said first force, for disengaging said packer setting means from said packer means.

14. An apparatus according to claim 13 wherein said packer means comprises:

a substantially elliptically configured elastomeric body;

a central surface extending circumferentially around said body and outwardly therefrom;

a plurality of ports defined through the central surface of said body;

a first tapered surface; and a second tapered surface, wherein said first and second tapered surfaces each extend in perpendicularly opposite directions from said central body and slope inwardly therefrom.

15. An apparatus according to claim 14 wherein said piston means comprises:

an inner surface in contact with at least one of said core samples;

a plurality of fluid loss channels; and a plurality of grooves formed into said inner surface for directing said clean fluid from said core samples into said fluid loss channels.

16. An apparatus according to claim 15 wherein said test apparatus further comprises:

a plurality of retaining inserts, insertable into said housing and in communication with said packer means;

a plurality of pressure inserts which communicate with said proppant bed such that the pressure and differential pressure therein can be measured;

a temperature insert in communication with said proppant bed such that the temperature thereof can be measured;

a plurality of proppant valve inserts for introducing said proppant slurry to said test apparatus; and a plurality of filtered flow inserts for introducing said clean fluid into, and removing said clean fluid from said test apparatus.

* * * * *